US012303198B2

(12) United States Patent
Xiao et al.

(10) Patent No.: US 12,303,198 B2
(45) Date of Patent: May 20, 2025

(54) METHOD AND APPARATUS FOR EVALUATING BLUE-LIGHT RADIATION INJURY TO RETINA, COMPUTER DEVICE, AND MEDIUM

(71) Applicant: BOE TECHNOLOGY GROUP CO., LTD., Beijing (CN)

(72) Inventors: Xiangchun Xiao, Beijing (CN); Fan Yang, Beijing (CN); Shengbao Dun, Beijing (CN)

(73) Assignee: BOE Technology Group Co., Ltd., Beijing (CN)

(*) Notice: Subject to any disclaimer, the term of this patent is extended or adjusted under 35 U.S.C. 154(b) by 510 days.

(21) Appl. No.: 17/801,977

(22) PCT Filed: Feb. 25, 2021

(86) PCT No.: PCT/CN2021/077906
§ 371 (c)(1),
(2) Date: Aug. 24, 2022

(87) PCT Pub. No.: WO2021/170039
PCT Pub. Date: Sep. 2, 2021

(65) Prior Publication Data
US 2023/0135360 A1     May 4, 2023

(30) Foreign Application Priority Data
Feb. 28, 2020   (CN) .......................... 202010128910.3

(51) Int. Cl.
*A61B 3/12* (2006.01)
*G09G 5/10* (2006.01)
*G16H 50/30* (2018.01)

(52) U.S. Cl.
CPC ................ *A61B 3/12* (2013.01); *G09G 5/10* (2013.01); *G16H 50/30* (2018.01); *G09G 2360/144* (2013.01)

(58) Field of Classification Search
CPC .... A61B 3/12; G09G 5/10; G09G 2320/0666; G09G 2360/144; G09G 2380/08; G16H 40/63; G16H 50/20; G16H 50/30
See application file for complete search history.

*Primary Examiner* — Jack Dinh
(74) *Attorney, Agent, or Firm* — WHDA, LLP

(57) ABSTRACT

A method and apparatus for evaluating blue-light-radiation injury to a retina, a computer device and a medium. The method includes: acquiring a current environmental brightness and a current middle-grayscale brightness of a displaying device; according to a weighted blue-light-radiation-exposure value of a current environment, current environmental brightness, a weighted blue-light-radiation-exposure value of displaying device and current middle-grayscale brightness of displaying device, determining a device-environment factor; according to device-environment factor and current environmental brightness, determining an optimum middle-grayscale brightness of the displaying device in the current environment; according to the current middle-grayscale brightness of displaying device, the optimum middle-grayscale brightness of the displaying device in the current environment and the weighted blue-light-radiation-exposure value of the current environment, determining a current retina weighted blue-light-radiation-exposure value; and according to comparison between the current retina weighted blue-light-radiation-exposure value and a retina blue-light maximum safety-tolerance value, determining whether an eye-protection safety standard is satisfied.

20 Claims, 4 Drawing Sheets

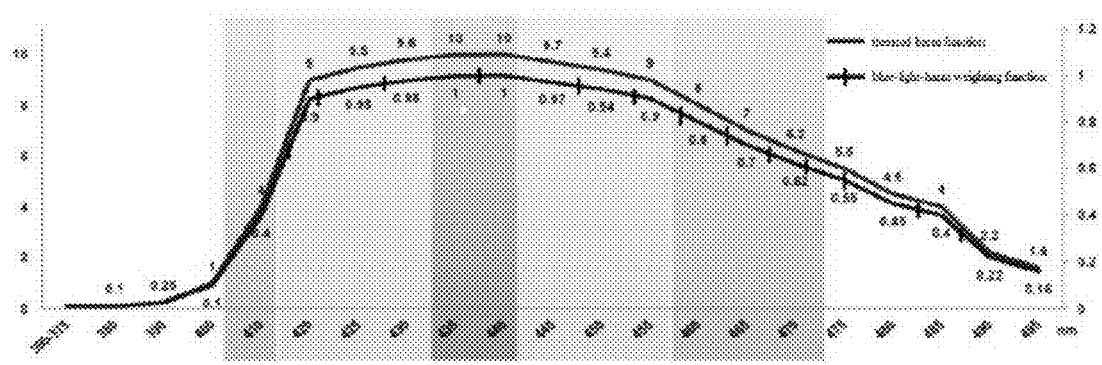
FIG. 2
| prototype | peak wavelength | 415-455nm power sum | 400-500 nm power sum | proportion |
|---|---|---|---|---|
| before improvement | 450nm | 0.1944 | 0.3562 | 54.6% |
| improvement 1 | 457nm | 0.1037 | 0.2995 | 34.6% |
| improvement 2 | 460nm | 0.1369 | 0.5193 | 26.4% |
FIG. 3
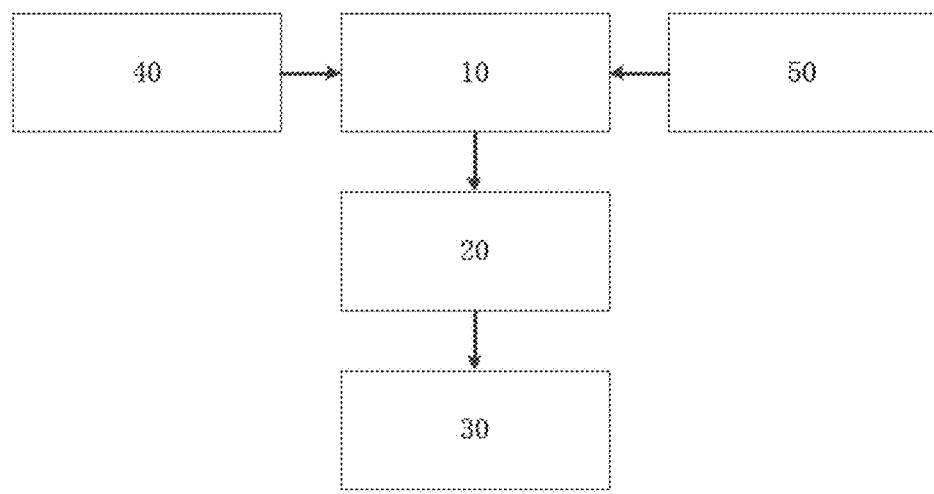
FIG. 4

METHOD AND APPARATUS FOR EVALUATING BLUE-LIGHT RADIATION INJURY TO RETINA, COMPUTER DEVICE, AND MEDIUM

CROSS REFERENCE TO RELEVANT APPLICATIONS

The present disclosure claims the priority of the Chinese patent application filed on Feb. 28, 2020 before the Chinese Patent Office with the application number of 202010128910.3 and the title of "METHOD AND APPARATUS FOR EVALUATING BLUE-LIGHT RADIATION INJURY TO RETINA, COMPUTER DEVICE, AND MEDIUM", which is incorporated herein in its entirety by reference.

TECHNICAL FIELD

The present disclosure relates to the technical field of displaying, and more particularly relates to a method and an apparatus for evaluating blue-light-radiation injury to a retina, a computer device and a medium.

BACKGROUND

In current standards for low-blue-light eye-protection displaying, there are generally two methods for reducing the injuring to the retina by blue light. One of them is reducing the color temperature, i.e., reducing the content of blue light in white light, thereby realizing the effect of reducing blue-light injury. The other method is, because the blue light that has the major injuring to human eyes is mainly the short-wavelength blue light (400 nm-450 nm), deviating the peak wavelength of the blue light toward the direction of the long wave, thereby reducing the injuring to human eyes by the short-wavelength blue light. Moreover, the eye-protection safety standard made accordingly refers to measuring the proportion of blue-light radiation in white light or the proportion of a blue light of a particular wave band in the spectrum of visible lights, to enable the proportions to satisfy preset standards.

However, the blue light in visible lights that truly injures the retina is the light that passes through the pupil and reaches the eye-base retina. Therefore, merely reducing the relative content of blue-light radiation may not ensure the absolute radiation quantity of the blue light that reaches the eye-base retina. For example, in a dark environment, the human-eye pupil expands, and the light input is in direct proportion to the square of the diameter of the pupil. However, in a brighter indoor official environment, the diameter of the human-eye pupil is smaller, and, therefore, in the same displaying brightness, the radiation quantity of the blue light that reaches the eye-base retina in a dark environment is considerably higher than the radiation quantity of the blue light that reaches the eye-base retina in an indoor official environment, and causes much higher injury to human eyes.

In order to promote sales, manufacturers of displaying devices have always tried to increase the brightness and the contrast of displaying devices to intensify visual stimulation, and propagandized that the displaying devices employ the technique of low blue light, and, by reducing the color temperature and/or deviating the peak wavelength of blue light toward the direction of the long wave, the displaying devices have the function of eye protection.

SUMMARY

The present disclosure provides a method and an apparatus for evaluating blue-light-radiation injury to a retina, a computer device and a medium.

The first aspect of the present disclosure provides a method for evaluating blue-light-radiation injury to a retina, wherein the method includes:

acquiring a current environmental brightness and a current middle-grayscale brightness of a displaying device;

according to a weighted blue-light-radiation-exposure value of a current environment, the current environmental brightness, a weighted blue-light-radiation-exposure value of the displaying device and the current middle-grayscale brightness of the displaying device, determining a device-environment factor;

according to the device-environment factor and the current environmental brightness, determining an optimum middle-grayscale brightness of the displaying device in the current environment;

according to the current middle-grayscale brightness of the displaying device, the optimum middle-grayscale brightness of the displaying device in the current environment and the weighted blue-light-radiation-exposure value of the current environment, determining a current retina weighted blue-light-radiation-exposure value; and according to comparison between the current retina weighted blue-light-radiation-exposure value and a retina blue-light maximum safety-tolerance value, determining whether an eye-protection safety standard is satisfied.

Optionally, the retina blue-light maximum safety-tolerance value is related to a weighted blue-light-radiation-exposure value of a standard environment.

Optionally, the step of, according to the weighted blue-light-radiation-exposure value of the current environment, the current environmental brightness, the weighted blue-light-radiation-exposure value of the displaying device and the current middle-grayscale brightness of the displaying device, determining the device-environment factor includes:

according to the weighted blue-light-radiation-exposure value $S_0$ of the current environment and the current environmental brightness $L_{environment}$, determining a brightness radiation-exposure coefficient $B_0$ of the current environment, wherein $B_0=S_0/L_{environment}$;

according to the weighted blue-light-radiation-exposure value S of the displaying device and the current middle-grayscale brightness $L_{mid}$ of the displaying device, determining a current brightness radiation-exposure coefficient B of the displaying device, wherein $B=S/L_{mid}$; and determining the device-environment factor H, wherein $H=B_0/B$.

Optionally, the step of, according to the device-environment factor and the current environmental brightness, determining the optimum middle-grayscale brightness of the displaying device in the current environment includes:

according to the device-environment factor H and the current environmental brightness $L_{environment}$, determining the optimum middle-grayscale brightness $L_{mids}$ of the displaying device in the current environment, wherein $L_{mids}=H*L_{environment}$.

Optionally, the step of, according to the current middle-grayscale brightness of the displaying device, the optimum middle-grayscale brightness of the displaying device in the current environment and the weighted blue-light-radiation-exposure value of the current environment, determining the current retina weighted blue-light-radiation-exposure value includes:

according to the current middle-grayscale brightness $L_{mid}$ of the displaying device, the optimum middle-grayscale brightness $L_{mids}$ of the displaying device in the current environment and the weighted blue-light-radiation-exposure value $S_0$ of the current environment, determining the current retina weighted blue-light-radiation-exposure value $S_1$, wherein $S_1=(L_{mid}/L_{mids})*S_0$.

Optionally, before the step of, according to the current middle-grayscale brightness $L_{mid}$ of the displaying device, the optimum middle-grayscale brightness $L_{mids}$ of the displaying device in the current environment and the weighted blue-light-radiation-exposure value $S_0$ of the current environment, determining the current retina weighted blue-light-radiation-exposure value $S_1$, wherein $S_1=(L_{mid}/L_{mids})*S_0$, the method further includes:

if the weighted blue-light-radiation-exposure value $S_0$ of the current environment is greater than the retina blue-light maximum safety-tolerance value $S_{max}$, setting a value of the weighted blue-light-radiation-exposure value $S_0$ of the current environment to be a value of the retina blue-light maximum safety-tolerance value $S_{max}$.

Optionally, the step of acquiring the current environmental brightness includes:

acquiring a background-wall illuminance of the displaying device; and according to the background-wall illuminance of the displaying device, determining an environmental brightness in a displaying environment, as the current environmental brightness.

Optionally, the step of acquiring the background-wall illuminance of the displaying device includes:

if a difference between the background-wall illuminance of the displaying device and a background-wall illuminance of a watching side is less than a preset threshold, detecting the background-wall illuminance of the watching side by using an optical sensor of the displaying device, and regarding the background-wall illuminance of the watching side as the background-wall illuminance of the displaying device.

Optionally, the step of acquiring the background-wall illuminance of the displaying device includes:

if a difference between the background-wall illuminance of the displaying device and a background-wall illuminance of a watching side is greater than a first preset threshold, detecting an illuminance of a background wall that is not blocked by the displaying device by using an optical sensor provided on a rear side of the displaying device, and regarding the illuminance as the background-wall illuminance of the displaying device.

Optionally, the step of acquiring the background-wall illuminance of the displaying device includes:

if a difference between the background-wall illuminance of the displaying device and a background-wall illuminance of a watching side is greater than a first preset threshold, by using an optical sensor disposed on a front side of the displaying device, collecting a first-illuminance equivalent electric-signal value $L_{xian0}$ of a facing background wall of a displaying position and a second-illuminance equivalent electric-signal value $L_{guan0}$ of a facing background wall of a watching position;

measuring a background-wall illuminance value $L_{ce}$ of the watching side when the displaying device is being normally used; and according to the first-illuminance equivalent electric-signal value $L_{xian0}$, the second-illuminance equivalent electric-signal value $L_{guan0}$ and the background-wall illuminance value $L_{ce}$ of the watching side, calculating a background-wall illuminance value $L_{xian}$ of the displaying device.

Optionally, the step of, according to the first-illuminance equivalent electric-signal value $L_{xian0}$, the second-illuminance equivalent electric-signal value $L_{guan0}$ and the background-wall illuminance value $L_{ce}$ of the watching side, calculating the background-wall illuminance value $L_{xian}$ of the displaying device includes:

according to a formula $L_{xian}=L_{ce}*L_{xian0}/L_{guan0}$, calculating the background-wall illuminance value $L_{xian}$ of the displaying device.

Optionally, the step of acquiring the background-wall illuminance of the displaying device includes:

if the background wall of the displaying device is in a complicated state, placing a standard white plate facing the displaying device at a watching position, and measuring a reflected-light illuminance of a region of the standard white plate that directly faces the displaying device; and regarding the reflected-light illuminance as the background-wall illuminance of the displaying device.

Optionally, the method further includes:

if it is determined that the eye-protection safety standard is satisfied, according to comparison between the current middle-grayscale brightness of the displaying device and the optimum middle-grayscale brightness of the displaying device in the current environment, determining a blue-light-hazard level of the displaying device.

Optionally, the step of, according to the comparison between the current middle-grayscale brightness of the displaying device and the optimum middle-grayscale brightness of the displaying device in the current environment, determining the blue-light-hazard level of the displaying device includes:

by regarding the optimum middle-grayscale brightness $L_{mids}$ of the displaying device in the current environment as a safety margin, performing blue-light-hazard-level judgement of the displaying device as follows:

$L_{mid} \leq 1.3 L_{mids}$ is a first level;

$1.3 L_{mids} \leq L_{mid} \leq 3.5 L_{mids}$ is a second level;

$3.5 L_{mids} \leq L_{mid} \leq 5 L_{mids}$ is a third level;

$5 L_{mids} \leq L_{mid} \leq 7 L_{mids}$ is a fourth level; and $7 L_{mids} \leq L_{mid}$ is a fifth level.

Optionally, the method further includes:

based on the blue-light-hazard level of the displaying device, performing brightness regulation to the displaying device.

Optionally, the step of, based on the blue-light-hazard level of the displaying device, performing brightness regulation to the displaying device includes:

if the blue-light-hazard level of the displaying device does not reach a standard level and the environmental brightness of the displaying environment is constant, regulating the current middle-grayscale brightness of the displaying device to have a difference with the environmental brightness of the displaying environment less than a second preset threshold.

Optionally, the step of, based on the blue-light-hazard level of the displaying device, performing brightness regulation to the displaying device includes:

if the blue-light-hazard level of the displaying device does not reach the standard level and the environmental brightness of the displaying environment varies, setting the current middle-grayscale brightness of the displaying device to change with the environmental brightness of the displaying environment in an equal proportion way.

Optionally, the weighted blue-light-radiation-exposure value of the current environment is determined based on a spectrum of a natural light that has a brightness equal to the current environmental brightness and a color temperature of D65; and the weighted blue-light-radiation-exposure value of the standard environment is determined based on a spectrum of a natural light that has a brightness of 400 nit and a color temperature of D65.

Optionally, the weighted blue-light-radiation-exposure value of the displaying device is determined based on a spectrum of the displaying device in a middle grayscale white frame.

The second aspect of the present disclosure provides a computer device, including a memory, a processor and a computer program that is stored in the memory and is executable in the processor, wherein when the processor executes the computer program, the method according to the first aspect of the present disclosure is capable of being implemented.

The third aspect of the present disclosure provides a nonvolatile computer-readable storage medium, storing a computer program, wherein when the computer program is executed by a processor, the method according to the first aspect of the present disclosure is capable of being implemented.

The fourth aspect of the present disclosure provides a computer program product, wherein the computer program product includes a computer-readable code, and when the computer-readable code is executed in a computer device, the computer-readable code causes the computer device to execute the method according to the first aspect of the present disclosure.

The above description is merely a summary of the technical solutions of the present disclosure. In order to more clearly know the elements of the present disclosure to enable the implementation according to the contents of the description, and in order to make the above and other purposes, features and advantages of the present disclosure more apparent and understandable, the particular embodiments of the present disclosure are provided below.

BRIEF DESCRIPTION OF THE DRAWINGS

In order to more clearly illustrate the technical solutions of the embodiments of the present disclosure or the related art, the particular embodiments of the present disclosure will be described in further detail below with reference to the drawings. Apparently, the figures that are described below are embodiments of the present disclosure, and a person skilled in the art may obtain other figures according to these figures without paying creative work.

FIG. 2 shows a curve diagram of the values of the blue-light-harm weighting function;

FIG. 3 shows a schematic diagram of the proportion of the harmful blue light after the peak wavelength of the blue light is deviated toward the direction of the long wave;

FIG. 4 shows a schematic diagram of the apparatus for evaluating blue-light-radiation injury to a retina according to an embodiment of the present disclosure;

DETAILED DESCRIPTION

Figure 1:
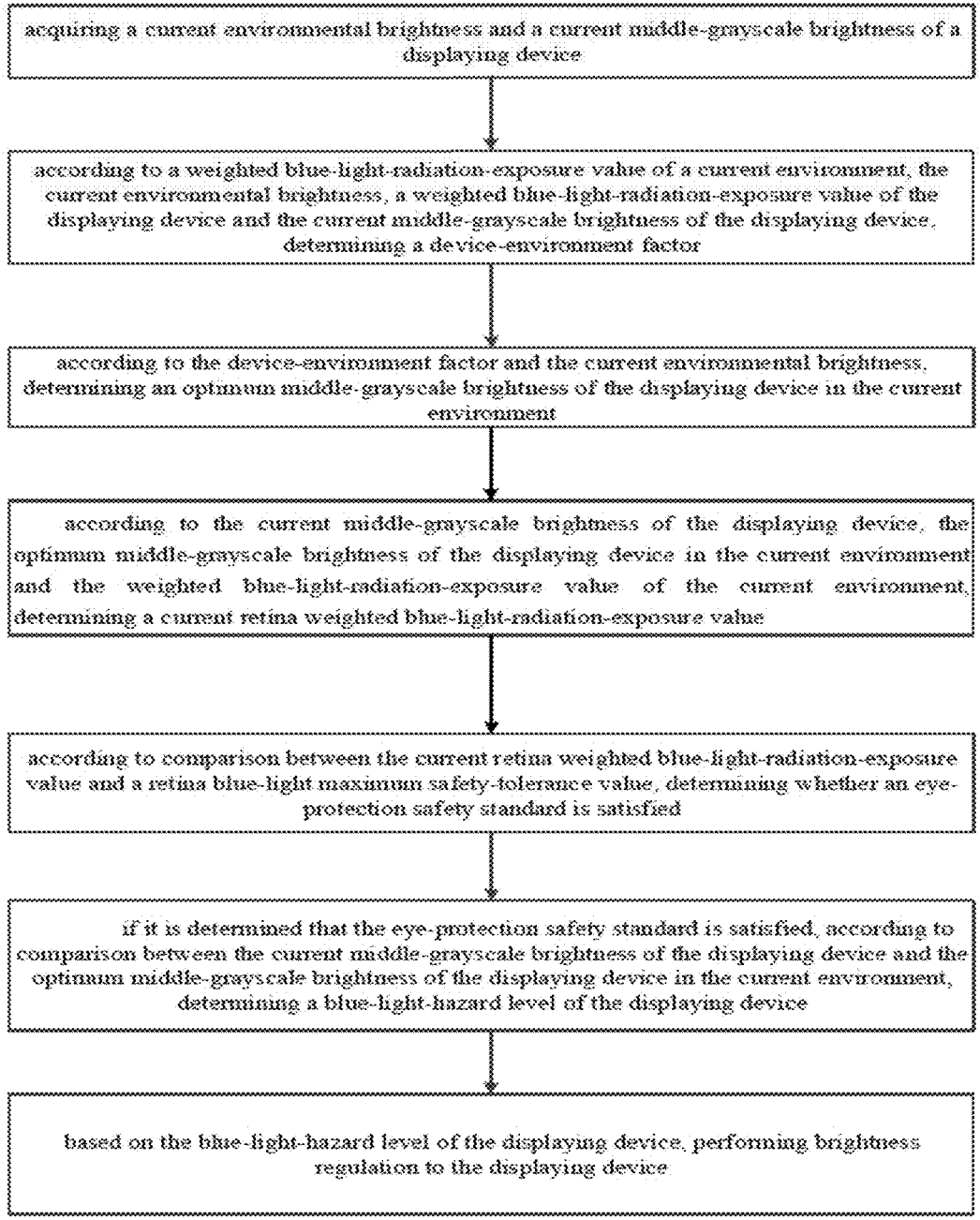
FIG. 1 shows a flow chart of the method for evaluating blue-light-radiation injury to a retina according to an embodiment of the present disclosure.

In order to more clearly illustrate the present disclosure, the present disclosure will be further described below with reference to the preferable embodiments and the drawings. The similar components in the drawings are indicated by the same reference numbers. A person skilled in the art should understand that the contents described particularly below are illustrative, rather than limiting, and should not be used to limit the protection scope of the present disclosure.

As shown in FIG. 1, an embodiment of the present disclosure provides a method for evaluating blue-light-radiation injury to a retina, including the first step to the fifth step, particularly as follows:

The first step: acquiring a current environmental brightness and a current middle-grayscale brightness of a displaying device.

The second step: according to a weighted blue-light-radiation-exposure value of a current environment, the current environmental brightness, a weighted blue-light-radiation-exposure value of the displaying device and the current middle-grayscale brightness of the displaying device, determining a device-environment factor.

It may be understood that the current environment refers to the current displaying environment or the displaying environment where the displaying device is currently located (for example, the interior of a living room, the interior of an office, and so on), and the weighted blue-light-radiation-exposure value of the displaying device refers to the weighted blue-light-radiation-exposure value of the displayed light of the displaying device.

The third step: according to the device-environment factor and the current environmental brightness, determining an optimum middle-grayscale brightness of the displaying device in the current environment.

The fourth step: according to the current middle-grayscale brightness of the displaying device, the optimum middle-grayscale brightness of the displaying device in the current environment and the weighted blue-light-radiation-exposure value of the current environment, determining a current retina weighted blue-light-radiation-exposure value.

The fifth step: according to comparison between the current retina weighted blue-light-radiation-exposure value and a retina blue-light maximum safety-tolerance value, determining whether an eye-protection safety standard is satisfied.

The method for evaluating blue-light-radiation injury to a retina according to the present embodiment, may realize accurate evaluation on the blue-light-radiation injury by the displaying device, which facilitates the protection to human eyes in combination with the weighted blue-light-radiation-exposure value of the current environment, the current environmental brightness, the weighted blue-light-radiation-exposure value of the displaying device and the current middle-grayscale brightness of the displaying device, and by regarding the absolute radiation quantity of the blue light reaching the eye-base retina as the eye-protection safety standard.

Regarding the First Step:

In some optional implementations of the present embodiment, the step of acquiring the current environmental brightness includes:

acquiring a background-wall illuminance of the displaying device; and according to the background-wall illuminance of the displaying device, determining an environmental brightness in a displaying environment, as the current environmental brightness.

The background-wall illuminance of the displaying device may be measured by using the following methods in different displaying environments, particularly including:

The first method: if a difference between the background-wall illuminance of the displaying device and a background-wall illuminance of a watching side is less than a preset threshold, detecting the background-wall illuminance of the watching side by using an optical sensor of the displaying device, and regarding the background-wall illuminance of the watching side as the background-wall illuminance of the displaying device.

The second method: if a difference between the background-wall illuminance of the displaying device and a background-wall illuminance of a watching side is greater than a first preset threshold, detecting an illuminance of a background wall that is not blocked by the displaying device by using an optical sensor provided on a rear side of the displaying device, and regarding the illuminance as the background-wall illuminance of the displaying device.

It may be understood that the top of the displaying device may refer to the position of the displaying device that is relatively upper, the front side of the displaying device may refer to the side of the displaying device that faces the watcher, and the rear side of the displaying device may refer to the side of the displaying device that is opposite to the front side; in other words, the rear side of the displaying device is back to the watcher. Therefore, that the optical sensor is disposed on the rear side of the displaying device refers to that the optical sensor is disposed on the side of the displaying device that is back to the watcher. The optical sensor may also be disposed on the rear side of the top of the displaying device; in other words, the optical sensor is disposed on the side of the displaying device that is back to the watcher, and is located at a position of the displaying device that is relatively upper. That may facilitate the optical sensor to detect the illuminance of the relatively upper position of the background wall that is not blocked by the displaying device.

The third method: if a difference between the background-wall illuminance of the displaying device and a background-wall illuminance of a watching side is greater than a first preset threshold, by using an optical sensor provided on a front side of the displaying device, collecting a first-illuminance equivalent electric-signal value $L_{xian0}$ of a facing background wall of a displaying position and a second-illuminance equivalent electric-signal value $L_{guan0}$ of a facing background wall of a watching position;

measuring a background-wall illuminance value $L_{ce}$ of the watching side when the displaying device is being normally used; and according to the first-illuminance equivalent electric-signal value $L_{xian0}$, the second-illuminance equivalent electric-signal value $L_{guan0}$ and the background-wall illuminance value $L_{ce}$ of the watching side, calculating a background-wall illuminance value $L_{xian}$ of the displaying device.

Optionally, the step of, according to the first-illuminance equivalent electric-signal value $L_{xian0}$, the second-illuminance equivalent electric-signal value $L_{guan0}$ and the background-wall illuminance value $L_{ce}$ of the watching side, calculating the background-wall illuminance value $L_{xian}$ of the displaying device includes:

according to a formula $L_{xian}=L_{ce}*L_{xian0}/L_{guan0}$, calculating the background-wall illuminance value $L_{xian}$ of the displaying device.

The fourth method: if a background wall of the displaying device is in a complicated state, placing a standard white plate facing the displaying device at a watching position, and measuring a reflected-light illuminance of a region of the standard white plate that directly faces the displaying device; and regarding the reflected-light illuminance as the background-wall illuminance of the displaying device.

Regarding the Second Step:

In some optional implementations of the present embodiment, the step of, according to the weighted blue-light-radiation-exposure value of the current environment, the current environmental brightness, the weighted blue-light-radiation-exposure value of the displaying device and the current middle-grayscale brightness of the displaying device, determining the device-environment factor includes:

according to the weighted blue-light-radiation-exposure value $S_0$ of the current environment and the current environmental brightness $L_{environment}$, determining a brightness radiation-exposure coefficient $B_0$ of the current environment, wherein $B_0=S_0/L_{environment}$, wherein $B_0$ characterizes the radiation quantity of the natural light in the current environment;

according to the weighted blue-light-radiation-exposure value $S$ of the displaying device and the current middle-grayscale brightness $L_{mid}$ of the displaying device, determining a current brightness radiation-exposure coefficient $B$ of the displaying device, wherein $B=S/L_{mid}$, wherein $B$ characterizes the current radiation quantity of the displaying device (i.e., the radiation quantity of the currently displayed light of the displaying device); and determining the device-environment factor $H$, wherein $H=B_0/B$.

Because different displaying environments result in different human-eye pupils, which in turn results in variation in the radiation intensity of the blue light received by the retina, in the present implementation, the device-environment factor $H$ is determined according to the variation and the relative radiation intensity of an optimum harmless spectrum, and may characterize the capacity of injuring of the blue light in the displayed light of the displaying device to human eyes in the current environmental brightness and displaying brightness.

In a particular example, the weighted blue-light-radiation-exposure value $S_0$ of the current environment is determined based on the spectrum of a natural light that has a brightness equal to the current environmental brightness $L_{environment}$ and a color temperature of D65. The D65 standard light source is also referred to as an International Standard Artificial Daylight, and has a color temperature of 6500K. The calculation formula of the weighted blue-light-radiation-exposure value $S_0$ of the current environment is: $S_0=\Sigma_{400}^{500} A_\lambda \cdot L_{environment, \lambda} \cdot \Delta\lambda$, wherein $A_\lambda$ refers to a weighted-blue-light-radiation-exposure-value coefficient or is referred to as a blue-light-injury factor or is referred to as a blue-light-harm weighting function, and $L_{environment}$ is obtained according to the spectrum of a natural light that has a brightness equal to the current environmental brightness $L_{environment}$ and a color temperature of D65, takes values being between 400 nm-500 nm with a step length of 1. The weighted blue-light-radiation-exposure value $S_0$ of the current environment characterizes the radiating capacity of the natural light in the current displaying environment. FIG. 2 shows the value curve of the blue-light-harm weighting function $A_\lambda$ in Photobiological Safety of Lamps and Lamp Systems of (GB\T20145-2006\CIE 5009\E:2002)/the State Standard of the People's Republic of China, from which the values of the blue-light-harm weighting function $A_\lambda$ may be obtained. In addition, the weighted blue-light-radiation-exposure value $S_0$ of the current environment may also be determined in the following manner: measuring the weighted blue-light-radiation-exposure value $S_{100}$ of the spectrum of a natural light that has a standard brightness $L_{100}$ (for example 100 nit) and a color temperature of D65, and then, according to the current environmental brightness $L_{environment}$, determining the weighted blue-light-radiation-exposure value $S_0$ of the current environment, wherein $S_0 = S_{100}*(L_{environment}/L_{100})$.

Continuing with the above particular example, the weighted blue-light-radiation-exposure value S of the displaying device is determined based on the spectrum of the displaying device in a middle grayscale white frame. The calculation formula of the weighted blue-light-radiation-exposure value S of the displaying device is: $S_0 = \Sigma_{400}^{500} A_\lambda \cdot L_{mid, \lambda} \cdot \Delta\lambda$, wherein $L_{mid,\lambda}$ is obtained according to the spectrum of the displaying device in a middle grayscale white frame. The weighted blue-light-radiation-exposure value S of the displaying device characterizes the radiating capacity of the displayed light (or, the displayed frame light) of the displaying device.

Regarding the third step and the fourth step:

In some optional implementations of the present embodiment, the weighted blue-light-radiation-exposure value of the standard environment is determined based on a spectrum of a natural light that has a brightness of 400 nit and a color temperature of D65.

The safety range given by the current IEC TR62471 is less than or equal to 1 W per square meter, which does not take into consideration the influence by the variation of the human-eye pupil in different environments. Because the current blue-light radiation standard is a relative standard, in the present implementation, the grading standard for goggles of the European Union is referred to. Starting from a typical environment, based on the spectrum of a D65 natural light of a brightness of 400 nit, its radiation-exposure value is regarded as the maximum harmless radiation-exposure value, which may improve the objectivity and the accuracy of the evaluation on the blue-light-radiation injury by the displaying device. It should be noted that, in a living room or a working environment, because the opening of the human-eye pupil is in the middle state, in this case the received radiation is high, and a light of the brightness of 400 nit may already generate a radiation injury similar to 2000 nit when the human-eye pupil is shrunk outdoor. Therefore, that radiation-exposure value may be selected to be the maximum harmless radiation-exposure value.

Optionally, the retina blue-light maximum safety-tolerance value is related to a weighted blue-light-radiation-exposure value of a standard environment.

In a particular example, the weighted blue-light-radiation-exposure value $S_{max}$ of the standard environment may be used as the retina blue-light maximum safety-tolerance value $S_{max}$. The weighted blue-light-radiation-exposure value $S_{max}$ of the standard environment characterizes a blue-light-radiation permissible value, and is determined according to the spectrum of a natural light that has a brightness of 400 nit and a color temperature of D65. The calculation formula of the weighted blue-light-radiation-exposure value $S_{max}$ of the standard environment is: $S_0 = \Sigma_{400}^{500} A_\lambda \cdot L_{standard, \lambda} \cdot \Delta\lambda$, wherein $L_{standard,\lambda}$ is obtained according to the spectrum of a natural light that has a brightness of 400 nit and a color temperature of D65. Certainly, the retina blue-light maximum safety-tolerance value $S_{max}$ may also be slightly greater than or less than the weighted blue-light-radiation-exposure value $S_{max}$ of the standard environment; for example, the proportion of the difference between them may be less than 5%. A person skilled in the art may set the relation between the weighted blue-light-radiation-exposure value $S_{max}$ of the standard environment and the retina blue-light maximum safety-tolerance value $S_{max}$ according to actual situations, which is not limited in the embodiments of the present disclosure.

In some optional implementations of the present embodiment, the step of, according to the device-environment factor and the current environmental brightness, determining the optimum middle-grayscale brightness of the displaying device in the current environment includes:

according to the device-environment factor H and the current environmental brightness $L_{environment}$, determining the optimum middle-grayscale brightness $L_{mids}$ of the displaying device in the current environment, wherein $L_{mids} = H*L_{environment}$.

In the present implementation, by using $S=S_0$ as the condition, the value of the optimum middle-grayscale brightness $L_{mids}$ of the displaying device is determined when the blue-light-radiation-exposure value of the displaying device is equal to that of the natural light in the current environment having a smallest injury to human eyes. If the value of the device-environment factor H is higher, that indicates a lower relative radiation of the displayed light of the displaying device, and accordingly the permitted displaying brightness is higher, wherein the device-environment factor H may characterize the brightness capacity of the displaying device. It should be noted that the "optimum" of the optimum middle-grayscale brightness of the displaying device in the current environment is with respect to the effect of eye protection, and is not for the effect of displaying.

In some optional implementations of the present embodiment, the step of, according to the current middle-grayscale brightness of the displaying device, the optimum middle-grayscale brightness of the displaying device in the current environment and the weighted blue-light-radiation-exposure value of the current environment, determining the current retina weighted blue-light-radiation-exposure value includes:

according to the current middle-grayscale brightness $L_{mid}$ of the displaying device, the optimum middle-grayscale brightness $L_{mids}$ of the displaying device in the current environment and the weighted blue-light-radiation-exposure value $S_0$ of the current environment, determining the current retina weighted blue-light-radiation-exposure value $S_1$, wherein $S_1 = (L_{mid}/L_{mids})*S_0$.

The present implementation may objectively and accurately determine the weighted blue-light-radiation-exposure values of the retina in the current environmental brightness and the displaying brightness.

In some optional implementations of the present embodiment, before the step of, according to the current middle-grayscale brightness $L_{mid}$ of the displaying device, the optimum middle-grayscale brightness $L_{mids}$ of the displaying device in the current environment and the weighted blue-light-radiation-exposure value $S_0$ of the current environment, determining the current retina weighted blue-lightradiation-exposure value $S_1$, wherein $S_1=(L_{mid}/L_{mids})*S_0$, the method further includes: if the weighted blue-light-radiation-exposure value $S_0$ of the current environment is greater than the retina blue-light maximum safety-tolerance value $S_{max}$, setting a value of the weighted blue-light-radiation-exposure value $S_0$ of the current environment to be a value of the retina blue-light maximum safety-tolerance value $S_{max}$.

If the determined weighted blue-light-radiation-exposure value $S_0$ of the current environment exceeds the retina blue-light maximum safety-tolerance value $S_{max}$, that indicates that the current displaying environment has already been a harmful optical environment, in which case the regulating power of human eyes themselves has already been unable to protect the retina from being injured. In this case, by using such an implementation, setting the value of $S_0$ to be $S_{max}$ may ensure the safety of displaying.

In some optional implementations of the present embodiment, after the fifth step, the method further includes:

The sixth step: if it is determined that the eye-protection safety standard is satisfied, according to comparison between the current middle-grayscale brightness of the displaying device and the optimum middle-grayscale brightness of the displaying device in the current environment, determining a blue-light-hazard level of the displaying device. In other words, if the current retina weighted blue-light-radiation-exposure value $S_1$ is less than the retina blue-light maximum safety-tolerance value $S_{max}$, the determination on the blue-light-hazard level of the displaying device is performed.

The present implementation may quantize the blue-light-hazard level of the displaying device in the current middle-grayscale brightness, and may realize objective, accurate and detailed evaluation to the blue-light-radiation injury by the displaying device, which facilitates the protection to human eyes.

In some optional implementations of the present embodiment, the step of, according to the comparison between the current middle-grayscale brightness of the displaying device and the optimum middle-grayscale brightness of the displaying device in the current environment, determining the blue-light-hazard level of the displaying device includes:

by regarding the optimum middle-grayscale brightness $L_{mids}$ of the displaying device in the current environment as a safety margin, performing blue-light-hazard-level judgement of the displaying device as follows:

$L_{mid} \leq 1.3L_{mids}$ is a first level; in other words, when $L_{mid} \leq 1.3L_{mids}$, it is determined that the blue-light-hazard level of the displaying device is the first level;

$L_{mid} \leq 1.3L_{mids}$ is a first level;

$1.3L_{mids} \leq L_{mid} \leq 3.5L_{mids}$ is a second level;

$3.5L_{mids} \leq L_{mid} \leq 5L_{mids}$ is a third level;

$5L_{mids} \leq L_{mid} \leq 7L_{mids}$ is a fourth level; and $7L_{mids} \leq L_{mid}$ is a fifth level. It may be understood that the first level is the optimum eye-protection level, the second level is the second optimum level, and the rest may be done in the same manner.

In some optional implementations of the present embodiment, after the sixth step, the method further includes:

The seventh step: based on the blue-light-hazard level of the displaying device, performing brightness regulation to the displaying device.

By regulating and controlling the brightness of the displayed light of the displaying device, the present implementation may enable the middle-grayscale brightness of the displaying device to approach the optimum middle-grayscale brightness $L_{mids}$ of the displaying device in the current environment. Whereby the radiation quantity of the blue light reaching the eye-base retina via the pupil is less than or close to the radiation quantity of the blue light of the natural light in the current environmental brightness to the largest extent, to ensure that the radiation intensity on the retina of the blue light in the displayed light is within the safety range, thereby realizing the protection to human eyes.

In a particular example, the brightness regulation should also take into consideration the demand on the effect of displaying (the image-quality level). In other words, the brightness regulation may be performed based on a comprehensive consideration of the blue-light-radiation-injury level and the effect of displaying, or the balance between them.

The blue-light-hazard level of the displaying device may be applied flexibly according to different demands. In a particular example, the second level (i.e., $L_{mid} \leq 3.5L_{mids}$) of the blue-light-hazard level of the displaying device is used as the standard, wherein if the level reaches the second level it is considered that the current middle-grayscale brightness of the displaying device satisfies the requirement, and if the level does not reach the second level it is considered that the current middle-grayscale brightness of the displaying device does not satisfy the requirement and the current middle-grayscale brightness of the displaying device is required to be reduced. Further, in a scene of a constant environmental brightness (for example, an indoor official scene where the illumination condition is constant), the current middle-grayscale brightness of the displaying device may be set to enable the displaying brightness of the displaying device to be close to the natural-light brightness of the displaying environment. In a scene where the environmental brightness is not constant, the current middle-grayscale brightness of the displaying device may be set to change with the brightness of the displaying environment in an equal proportion way.

For example, the brightness for the displaying device to maintain the middle grayscale is $L_{127}$ (the grayscale of the maximum brightness is $L_{255}$), and then the maximum brightness of the displaying device $L_{max}=L_{127}*2^\gamma$, wherein $\gamma$ is the index of the brightness curve, whose value is generally approximately 2.2 in an indoor environment. In a scene of a constant environmental brightness, if the brightness of the displaying environment is 50 nit, then the brightness $L_{127}$ for the displaying device to maintain the middle grayscale is set to be 50 nit, and accordingly $L_{max}=230$ nit. Moreover, the maximum brightness of the display screen of common television sets is set to be approximately 350 nit to 450 nit. Therefore, by using the mode of regulation according to the present embodiment, the blue-light radiation quantity may be reduced by ⅓-½. Further, the color temperature of the display screen of the television set may be maintained at 6700K, whereby the color temperature of the displayed frame is substantially equal to the color temperature of the natural light, to maintain a nature-like state, and ensure the effect of displaying. Further, the peak wavelength of the blue light may be deviated toward the direction of the long wave. In other words, the peak value of the blue-light light source of the display screen of the television set is moved in the direction of the long wave, to reduce the proportion of the harmful blue light, as shown in FIG. 3.

It may be understood that the method for evaluating blue-light-radiation injury to a retina according to the present embodiment may also be applied for visible lights of other frequency spectrums.

As shown in FIG. 4, another embodiment of the present disclosure provides an apparatus for evaluating blue-light-radiation injury to a retina, wherein the apparatus includes:

an acquiring module 10 configured for acquiring a current environmental brightness and a current middle-grayscale brightness of a displaying device;

a calculating module 20 configured for, according to a weighted blue-light-radiation-exposure value of a current environment, the current environmental brightness, a weighted blue-light-radiation-exposure value of the displaying device and the current middle-grayscale brightness of the displaying device, determining a device-environment factor; and by using the weighted blue-light-radiation-exposure value of the standard environment as the retina blue-light maximum safety-tolerance value, according to the device-environment factor and the current environmental brightness, determining an optimum middle-grayscale brightness of the displaying device in the current environment, and according to the current middle-grayscale brightness of the displaying device, the optimum middle-grayscale brightness of the displaying device in the current environment and the weighted blue-light-radiation-exposure value of the current environment, determining a current retina weighted blue-light-radiation-exposure value; and an evaluating module 30 configured for, according to comparison between the current retina weighted blue-light-radiation-exposure value and a retina blue-light maximum safety-tolerance value, determining whether an eye-protection safety standard is satisfied.

In some optional implementations of the present embodiment, as shown in FIG. 4, the apparatus further includes a luminance sensor 40 for sensing the current environmental brightness and a memory 50 for storing a constant environmental brightness. Regarding a scene where the brightness of the displaying environment is not constant, the luminance sensor 40 may be used to sense the current environmental brightness in real time. Regarding a scene where the brightness of the displaying environment is constant, the acquiring module 10 may read the stored constant environmental brightness from the memory 50 as the current environmental brightness.

It should be noted that the principle and the working process of the apparatus for evaluating blue-light-radiation injury to a retina according to the present embodiment are similar to those of the method for evaluating blue-light-radiation injury to a retina stated above, and the related parts may refer to the above description, and are not discussed here further.

Figure 5:
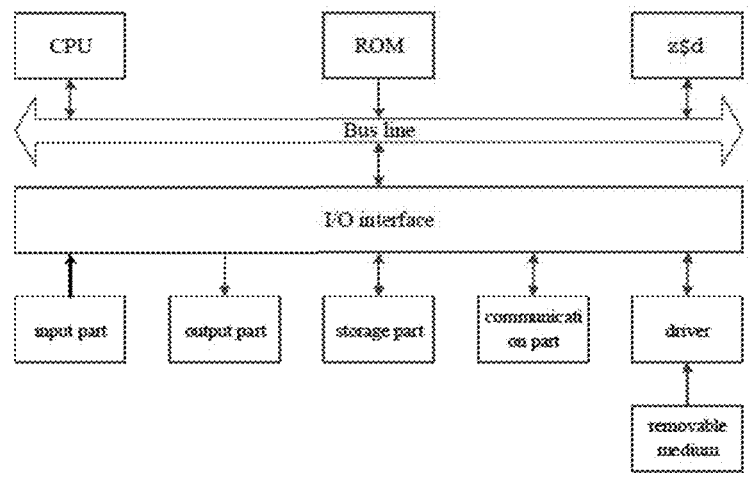
FIG. 5 shows a schematic structural diagram of the apparatus for evaluating blue-light-radiation injury to a retina according to an embodiment of the present disclosure.

As shown in FIG. 5, a computer system adapted for implementing the apparatus for evaluating blue-light-radiation injury to a retina according to the present embodiment includes a central processing module (CPU), which may perform various proper actions and processes according to a program stored in a read-only memory (ROM) or a program loaded from a storage part to a random access memory (RAM). The RAM further stores various programs and data that are required by the operation of the computer system. The CPU, the ROM and the RAM are interconnected by a bus line. An input/output (I/O) interface is also connected to the bus line.

The following components are connected to the I/O interface: an input part, including a keyboard, a mouse and so on; an output part, including a liquid-crystal display (LCD), a loudspeaker and so on; a storage part, including a hard disk and so on; and a communication part, including for example a LAN card and a network interface card of a modem and so on. The communication part performs communication processing via a network such as Internet. A driver is also connected to the I/O interface according to demands. A removable medium, such as a magnetic disk, an optical disc, a magneto-optical disk, a semiconductor memory and so on, is installed on the driver according to demands, so as to install the computer program read therefrom into the storage part according to demands.

Particularly, according to the present embodiment, the process illustrated in the above flow chart may be realized as a computer software program. For example, the present embodiment includes a computer program product, which includes a computer program tangibly contained in a computer-readable medium, and the computer program includes a program code for executing method shown in the flow chart. In such an embodiment, the computer program may be downloaded and installed from a network by using the communication part, and/or be installed from the removable medium.

The flow charts and the schematic diagrams of the drawings illustrate the system architectures, functions and operations that may be realized by the system, the method and the computer program product according to the present embodiment. In this regard, each of the blocks in the flow charts or the schematic diagrams may represent part of a module, a program segment or a code, and the part of the module, the program segment or the code contains one or more executable instructions for performing specified logic functions. Further, it should be noted that, in some alternative implementations, the functions marked in the blocks may also be performed in a sequence that is different from that marked in the drawings. For example, two blocks illustrated in succession may actually be executed substantially concurrently, and they sometimes may also be executed in an opposite sequence, which depends on the involved functions. Furthermore, it should be noted that each of the blocks in the schematic diagrams and/or the flow charts, and a combination of the blocks in the schematic diagrams and/or the flow charts, may be implemented by using a dedicated hardware-based system for performing specified functions or operations, or may be implemented by using a combination of a dedicated hardware and a computer instruction.

The modules described in the present embodiment may be implemented as software, and may also be implemented as hardware. The described modules may also be provided in a processor; for example, they may be described as: a processor, containing an acquiring module, a calculating module and an evaluating module. The names of those modules do not function as a limitation on the modules themselves under certain circumstances. For example, the evaluating module may also be described as a "judging module".

As another aspect, the present embodiment further provides a nonvolatile computer storage medium. The nonvolatile computer storage medium may be a nonvolatile computer storage medium that is contained in the apparatus according to the above embodiments, and may also be a nonvolatile computer storage medium that stands alone and has not been installed into a terminal. The nonvolatile computer storage medium stores one or more programs, and the one or more programs, when executed by a device, cause the device to perform the operations of: acquiring a current environmental brightness and a current middle-grayscale brightness of a displaying device; according to a weighted blue-light-radiation-exposure value of a current environment, the current environmental brightness, a weighted blue-light-radiation-exposure value of the displaying device and the current middle-grayscale brightness of the displaying device, determining a device-environment factor; by using the weighted blue-light-radiation-exposure value of the standard environment as the retina blue-light maximum safety-tolerance value, according to the device-environment factor and the current environmental brightness, determining an optimum middle-grayscale brightness of the displaying device in the current environment, and according to the current middle-grayscale brightness of the displaying device, the optimum middle-grayscale brightness of the displaying device in the current environment and the weighted blue-light-radiation-exposure value of the current environment, determining a current retina weighted blue-light-radiation-exposure value; and according to comparison between the current retina weighted blue-light-radiation-exposure value and a retina blue-light maximum safety-tolerance value, determining whether an eye-protection safety standard is satisfied.

The above-described device embodiments are merely illustrative, wherein the units that are described as separate components may or may not be physically separate, and the components that are displayed as units may or may not be physical units; in other words, they may be located at the same one location, and may also be distributed to a plurality of network units. Some or all of the modules may be selected according to the actual demands to realize the purposes of the solutions of the embodiments. A person skilled in the art may understand and implement the technical solutions without paying creative work.

Each component embodiment of the present disclosure may be implemented by hardware, or by software modules that are operated on one or more processors, or by a combination thereof. A person skilled in the art should understand that some or all of the functions of some or all of the components of the computer device according to the embodiments of the present disclosure may be implemented by using a microprocessor or a digital signal processor (DSP) in practice. The present disclosure may also be implemented as apparatus or device programs (for example, computer programs and computer program products) for implementing part of or the whole of the method described herein. Such programs for implementing the present disclosure may be stored in a computer-readable medium, or may be in the form of one or more signals. Such signals may be downloaded from an Internet website, or provided on a carrier signal, or provided in any other forms.

Figure 6:
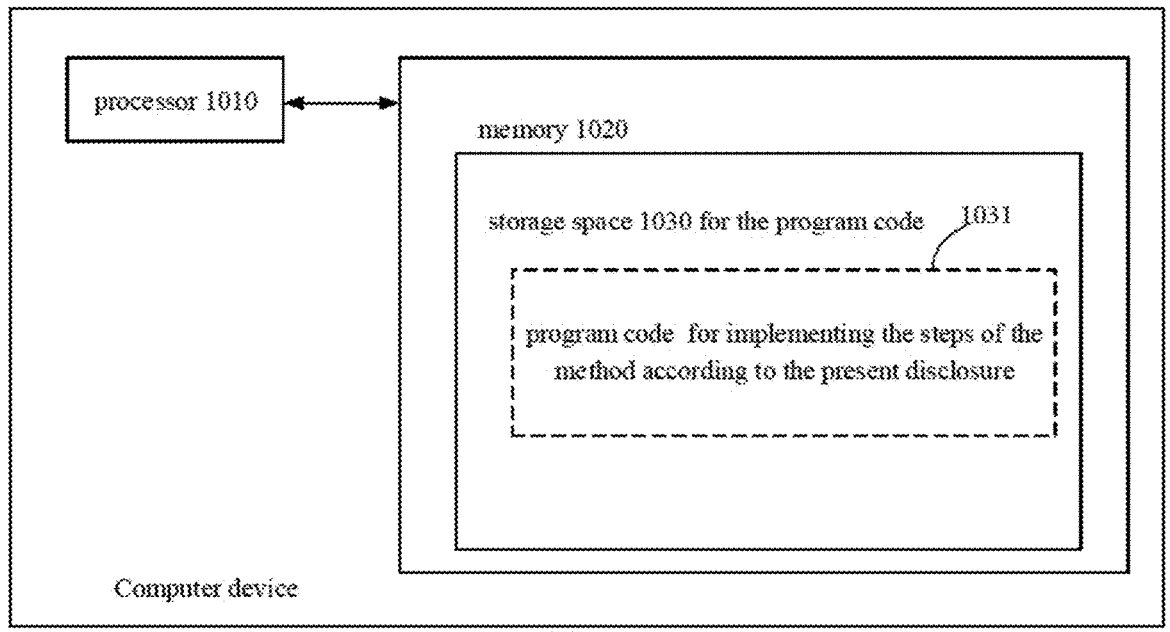
FIG. 6 schematically shows a block diagram of a computer device for executing the method according to the present disclosure.
Figure 7:
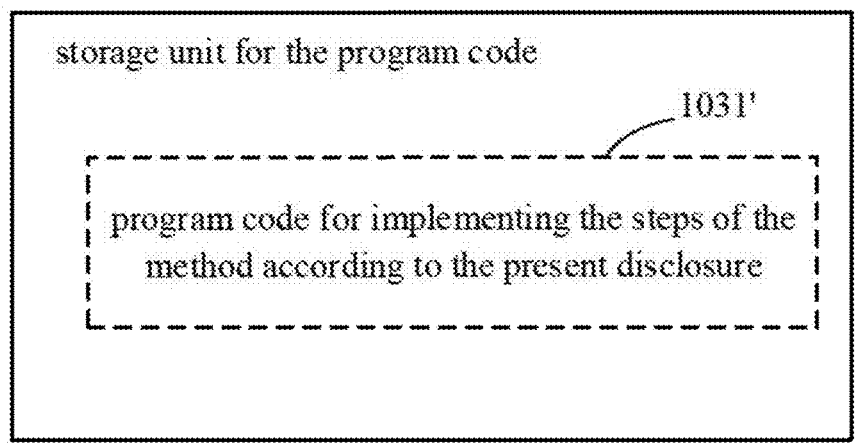
FIG. 7 schematically shows a storage unit for maintaining or carrying a program code for executing the method according to the present disclosure.

For example, FIG. 6 shows a computer device that may implement the method according to the present disclosure. The computer device traditionally includes a processor 1010 and a computer program product or computer-readable medium in the form of a memory 1020. The memory 1020 may be electronic memories such as flash memory, EEPROM (Electrically Erasable Programmable Read Only Memory), EPROM, hard disk or ROM. The memory 1020 has the storage space 1030 of the program code 1031 for implementing any steps of the above method. For example, the storage space 1030 for program code may contain program codes 1031 for individually implementing each of the steps of the above method. Those program codes may be read from one or more computer program products or be written into the one or more computer program products. Those computer program products include program code carriers such as a hard disk, a compact disk (CD), a memory card or a floppy disk. Such computer program products are usually portable or fixed storage units as shown in FIG. 7. The storage unit may have storage segments or storage spaces with similar arrangement to the memory 1020 of the computer device in FIG. 6. The program codes may, for example, be compressed in a suitable form. Generally, the storage unit contains a computer-readable code 1031', which may be read by a processor like 1010. When those codes are executed by the computer device, the codes cause the computer device to implement each of the steps of the method described above.

In the description of the present disclosure, it should be noted that the terms "include", "comprise" or any variants thereof are intended to cover non-exclusive inclusions, so that processes, methods, articles or devices that include a series of elements do not only include those elements, but also include other elements that are not explicitly listed, or include the elements that are inherent to such processes, methods, articles or devices. Unless further limitation is set forth, an element defined by the wording "comprising a . . . " does not exclude additional same element in the process, method, article or device comprising the element. The word "a" or "an" preceding an element does not exclude the existing of a plurality of such elements. The present disclosure may be implemented by means of hardware comprising several different elements and by means of a properly programmed computer. In unit claims that list several devices, some of those devices may be embodied by the same item of hardware. The words first, second, third and so on do not denote any order. Those words may be interpreted as names.

The "one embodiment", "an embodiment" or "one or more embodiments" as used herein means that particular features, structures or characteristics described with reference to an embodiment are included in at least one embodiment of the present disclosure. Moreover, it should be noted that here an example using the wording "in an embodiment" does not necessarily refer to the same one embodiment.

The description provided herein describes many concrete details. However, it may be understood that the embodiments of the present disclosure may be implemented without those concrete details. In some of the embodiments, well-known processes, structures and techniques are not described in detail, so as not to affect the understanding of the description.

Apparently, the above embodiments of the present disclosure are merely examples that are made for clearly describing the present disclosure, and are not limitation on the embodiments of the present disclosure, and a person skilled in the art may make other variations or modifications in different forms on the basis of the above description. The embodiments cannot be exhaustively listed herein, and all of the obvious variations or modifications that are made on the basis of the technical solutions of the present disclosure still fall within the protection scope of the present disclosure.

The invention claimed is:

1. A method for evaluating blue-light-radiation injury to a retina, wherein the method comprises:
acquiring a current environmental brightness and a current middle-grayscale brightness of a displaying device;
according to a weighted blue-light-radiation-exposure value of a current environment, the current environmental brightness, a weighted blue-light-radiation-exposure value of the displaying device and the current middle-grayscale brightness of the displaying device, determining a device-environment factor;
according to the device-environment factor and the current environmental brightness, determining an optimum middle-grayscale brightness of the displaying device in the current environment;
according to the current middle-grayscale brightness of the displaying device, the optimum middle-grayscale brightness of the displaying device in the current environment and the weighted blue-light-radiation-exposure value of the current environment, determining a current retina weighted blue-light-radiation-exposure value; and according to comparison between the current retina weighted blue-light-radiation-exposure value and a retina blue-light maximum safety-tolerance value, determining whether an eye-protection safety standard is satisfied.

2. The method according to claim 1, wherein the retina blue-light maximum safety-tolerance value is related to a weighted blue-light-radiation-exposure value of a standard environment.

3. The method according to claim 1, wherein the step of, according to the weighted blue-light-radiation-exposure value of the current environment, the current environmental brightness, the weighted blue-light-radiation-exposure value of the displaying device and the current middle-grayscale brightness of the displaying device, determining the device-environment factor comprises:

according to the weighted blue-light-radiation-exposure value $S_0$ of the current environment and the current environmental brightness $L_{environment}$, determining a brightness radiation-exposure coefficient $B_0$ of the current environment, wherein $B_0=S_0/L_{environment}$;

according to the weighted blue-light-radiation-exposure value S of the displaying device and the current middle-grayscale brightness $L_{mid}$ of the displaying device, determining a current brightness radiation-exposure coefficient B of the displaying device, wherein $B=S/L_{mid}$; and determining the device-environment factor H, wherein $H=B_0/B$.

4. The method according to claim 3, wherein the step of, according to the device-environment factor and the current environmental brightness, determining the optimum middle-grayscale brightness of the displaying device in the current environment comprises:

according to the device-environment factor H and the current environmental brightness $L_{environment}$, determining the optimum middle-grayscale brightness $L_{mids}$ of the displaying device in the current environment, wherein $L_{mids}=H*L_{environment}$.

5. The method according to claim 4, wherein the step of, according to the current middle-grayscale brightness of the displaying device, the optimum middle-grayscale brightness of the displaying device in the current environment and the weighted blue-light-radiation-exposure value of the current environment, determining the current retina weighted blue-light-radiation-exposure value comprises:

according to the current middle-grayscale brightness $L_{mid}$ of the displaying device, the optimum middle-grayscale brightness $L_{mids}$ of the displaying device in the current environment and the weighted blue-light-radiation-exposure value $S_0$ of the current environment, determining the current retina weighted blue-light-radiation-exposure value $S_1$, wherein $S_1=(L_{mid}/L_{mids})*S_0$.

6. The method according to claim 5, wherein before the step of, according to the current middle-grayscale brightness $L_{mid}$ of the displaying device, the optimum middle-grayscale brightness $L_{mids}$ of the displaying device in the current environment and the weighted blue-light-radiation-exposure value $S_0$ of the current environment, determining the current retina weighted blue-light-radiation-exposure value $S_1$, wherein $S_1=(L_{mid}/L_{mids})*S_0$, the method further comprises:

if the weighted blue-light-radiation-exposure value $S_0$ of the current environment is greater than the retina blue-light maximum safety-tolerance value $S_{max}$, setting a value of the weighted blue-light-radiation-exposure value $S_0$ of the current environment to be a value of the retina blue-light maximum safety-tolerance value $S_{max}$.

7. The method according to claim 1, wherein the step of acquiring the current environmental brightness comprises:

acquiring a background-wall illuminance of the displaying device; and according to the background-wall illuminance of the displaying device, determining an environmental brightness in a displaying environment, as the current environmental brightness;

wherein the step of acquiring the background-wall illuminance of the displaying device comprises:

if a difference between the background-wall illuminance of the displaying device and a background-wall illuminance of a watching side is less than a preset threshold, detecting the background-wall illuminance of the watching side by using an optical sensor of the displaying device, and regarding the background-wall illuminance of the watching side as the background-wall illuminance of the displaying device.

8. The method according to claim 7, wherein the step of acquiring the background-wall illuminance of the displaying device comprises:

if a difference between the background-wall illuminance of the displaying device and a background-wall illuminance of a watching side is greater than a first preset threshold, detecting an illuminance of a background wall that is not blocked by the displaying device by using an optical sensor disposed on a rear side of the displaying device, and regarding the illuminance as the background-wall illuminance of the displaying device.

9. The method according to claim 7, wherein the step of acquiring the background-wall illuminance of the displaying device comprises:

if a difference between the background-wall illuminance of the displaying device and a background-wall illuminance of a watching side is greater than a first preset threshold, by using an optical sensor disposed on a front side of the displaying device, collecting a first-illuminance equivalent electric-signal value $L_{xian0}$ of a facing background wall of a displaying position and a second-illuminance equivalent electric-signal value $L_{guan0}$ of a facing background wall of a watching position;

measuring a background-wall illuminance value $L_{ce}$ of the watching side when the displaying device is being normally used; and according to the first-illuminance equivalent electric-signal value $L_{xian0}$, the second-illuminance equivalent electric-signal value $L_{guan0}$ and the background-wall illuminance value $L_{ce}$ of the watching side, calculating a background-wall illuminance value $L_{xian}$ of the displaying device.

10. The method according to claim 9, wherein the step of, according to the first-illuminance equivalent electric-signal value $L_{xian0}$, the second-illuminance equivalent electric-signal value $L_{guan0}$ and the background-wall illuminance value $L_{ce}$ of the watching side, calculating the background-wall illuminance value $L_{xian}$ of the displaying device comprises:

according to a formula $L_{xian}=L_{ce}*L_{xian0}/L_{guan0}$, calculating the background-wall illuminance value $L_{xian}$ of the displaying device.

11. The method according to claim 7, wherein the step of acquiring the background-wall illuminance of the displaying device comprises:
   if the background wall of the displaying device is in a complicated state, placing a standard white plate facing the displaying device at a watching position, and measuring a reflected-light illuminance of a region of the standard white plate that directly faces the displaying device; and
   regarding the reflected-light illuminance as the background-wall illuminance of the displaying device.

12. The method according to claim 1, wherein the method further comprises:
   if it is determined that the eye-protection safety standard is satisfied, according to comparison between the current middle-grayscale brightness of the displaying device and the optimum middle-grayscale brightness of the displaying device in the current environment, determining a blue-light-hazard level of the displaying device.

13. The method according to claim 12, wherein the step of, according to the comparison between the current middle-grayscale brightness of the displaying device and the optimum middle-grayscale brightness of the displaying device in the current environment, determining the blue-light-hazard level of the displaying device comprises:
   by regarding the optimum middle-grayscale brightness $L_{mids}$ of the displaying device in the current environment as a safety margin, performing blue-light-hazard-level judgement of the displaying device as follows:
   $L_{mid} \leq 1.3 L_{mids}$ is a first level;
   $1.3 L_{mids} < L_{mid} \leq 3.5 L_{mids}$ is a second level;
   $3.5 L_{mids} < L_{mid} \leq 5 L_{mids}$ is a third level;
   $5 L_{mids} < L_{mid} \leq 7 L_{mids}$ is a fourth level; and
   $7 L_{mids} < L_{mid}$ is a fifth level.

14. The method according to claim 12, wherein the method further comprises:
   based on the blue-light-hazard level of the displaying device, performing brightness regulation to the displaying device.

15. The method according to claim 14, wherein the step of, based on the blue-light-hazard level of the displaying device, performing brightness regulation to the displaying device comprises:
   if the blue-light-hazard level of the displaying device does not reach a standard level and the environmental brightness of the displaying environment is constant, regulating the current middle-grayscale brightness of the displaying device to have a difference with the environmental brightness of the displaying environment less than a second preset threshold.

16. The method according to claim 15, wherein the step of, based on the blue-light-hazard level of the displaying device, performing brightness regulation to the displaying device comprises:
   if the blue-light-hazard level of the displaying device does not reach the standard level and the environmental brightness of the displaying environment varies, setting the current middle-grayscale brightness of the displaying device to change with the environmental brightness of the displaying environment in an equal proportion way.

17. The method according to claim 1, wherein the weighted blue-light-radiation-exposure value of the current environment is determined based on a spectrum of a natural light that has a brightness equal to the current environmental brightness and a color temperature of D65; and
   the weighted blue-light-radiation-exposure value of the standard environment is determined based on a spectrum of a natural light that has a brightness of 400 nit and a color temperature of D65.

18. The method according to claim 1, wherein the weighted blue-light-radiation-exposure value of the displaying device is determined based on a spectrum of the displaying device in a middle grayscale white frame.

19. A computer device, comprising a memory, a processor and a computer program that is stored in the memory and is executable in the processor, wherein when the processor executes the computer program, the method according to claim 1 is capable of being implemented.

20. A non-transitory computer-readable storage medium, storing a computer program, wherein when the computer program is executed by a processor, the method according to claim 1 is capable of being implemented.

* * * * *